United States Patent
Condie et al.

(10) Patent No.: US 9,060,778 B2
(45) Date of Patent: Jun. 23, 2015

(54) INTERMITTENT SHORT CIRCUIT DETECTION ON A MULTI-ELECTRODE CATHETER

(75) Inventors: Catherine R. Condie, Shoreview, MN (US); Marshall L. Sherman, Cardiff by the Sea, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 466 days.

(21) Appl. No.: 13/456,592

(22) Filed: Apr. 26, 2012

(65) Prior Publication Data

US 2013/0289551 A1    Oct. 31, 2013

(51) Int. Cl.
*A61B 18/18* (2006.01)
*A61B 18/12* (2006.01)
*A61B 18/00* (2006.01)
*A61B 18/14* (2006.01)

(52) U.S. Cl.
CPC ... *A61B 18/1233* (2013.01); *A61B 2018/00345* (2013.01); *A61B 2018/00351* (2013.01); *A61B 2018/00577* (2013.01); *A61B 2018/00642* (2013.01); *A61B 2018/00672* (2013.01); *A61B 2018/00708* (2013.01); *A61B 2018/00875* (2013.01); *A61B 2018/00898* (2013.01); *A61B 18/1492* (2013.01); *A61B 2018/00267* (2013.01); *A61B 2018/00654* (2013.01); *A61B 2018/1435* (2013.01)

(58) Field of Classification Search
USPC .............................. 606/32, 34, 40.38, 45–52
See application file for complete search history.

(56) References Cited

U.S. PATENT DOCUMENTS

| 5,514,129 | A | 5/1996 | Smith |
| 5,681,308 | A | 10/1997 | Edwards et al. |
| 5,769,846 | A | 6/1998 | Edwards et al. |
| 5,897,577 | A | 4/1999 | Cinbis et al. |
| 6,050,267 | A | 4/2000 | Nardella et al. |
| 6,132,426 | A * | 10/2000 | Kroll .............. 606/41 |
| 6,203,541 | B1 | 3/2001 | Keppel |
| 6,217,574 | B1 | 4/2001 | Webster |
| 6,256,540 | B1 | 7/2001 | Panescu et al. |
| 6,391,024 | B1 | 5/2002 | Sun et al. |
| 6,546,270 | B1 | 4/2003 | Goldin et al. |
| 6,730,079 | B2 | 5/2004 | Lovewell |
| 7,736,357 | B2 | 6/2010 | Lee, Jr. et al. |
| 8,398,626 | B2 * | 3/2013 | Buysse et al. .......... 606/34 |
| 2002/0032439 | A1 | 3/2002 | Hareyama |
| 2004/0064161 | A1 | 4/2004 | Gunderson et al. |

(Continued)

FOREIGN PATENT DOCUMENTS

| EP | 1151725 A1 | 11/2001 |
| EP | 1429678 B1 | 3/2006 |

(Continued)

*Primary Examiner* — Paula J Stice
(74) *Attorney, Agent, or Firm* — Christopher & Weisberg, P.A.

(57) ABSTRACT

A method and system for detecting a short circuit during a radiofrequency ablation procedure. The method includes measuring an impedance of a pair of electrodes coupled to a treatment assembly of a medical device. Radiofrequency ablation energy is transmitted between the pair of electrodes. The transmission of radiofrequency ablation energy between the pair of electrodes is terminated when after a predetermined period of time the measured impedance in either of the electrodes in the pair of electrodes is below a predetermined threshold impedance value. An alert is generated indicating a short circuit between the pair of electrodes.

16 Claims, 9 Drawing Sheets

(56) References Cited

U.S. PATENT DOCUMENTS

| | | |
|---|---|---|
| 2005/0222562 A1 | 10/2005 | Lovewell |
| 2005/0283074 A1 | 12/2005 | Jackson et al. |
| 2007/0062547 A1 | 3/2007 | Pappone |
| 2007/0173808 A1 | 7/2007 | Goble |
| 2008/0281312 A1 | 11/2008 | Werneth et al. |
| 2008/0281314 A1 | 11/2008 | Johnson et al. |
| 2009/0030664 A1 | 1/2009 | Bridges et al. |
| 2009/0240244 A1 | 9/2009 | Malis et al. |
| 2009/0275827 A1 | 11/2009 | Aiken et al. |
| 2010/0049188 A1 | 2/2010 | Nelson et al. |
| 2010/0168557 A1 | 7/2010 | Deno et al. |
| 2010/0168571 A1 | 7/2010 | Savery et al. |
| 2010/0179538 A1 | 7/2010 | Podhajsky |
| 2010/0274238 A1 | 10/2010 | Klimovitch |
| 2011/0046618 A1 | 2/2011 | Minar et al. |
| 2011/0130755 A1 | 6/2011 | Bhushan et al. |
| 2011/0144524 A1 | 6/2011 | Fish et al. |
| 2011/0152712 A1 | 6/2011 | Cao et al. |
| 2011/0230876 A1 | 9/2011 | Hong et al. |
| 2011/0270243 A1 | 11/2011 | Skarda et al. |
| 2012/0265194 A1 | 10/2012 | Podhajsky |

FOREIGN PATENT DOCUMENTS

| | | |
|---|---|---|
| EP | 1803410 A1 | 7/2007 |
| EP | 1867279 A3 | 12/2007 |
| EP | 1280467 B1 | 11/2008 |
| WO | 2004011090 A2 | 2/2004 |
| WO | 2011103129 A2 | 8/2011 |

* cited by examiner

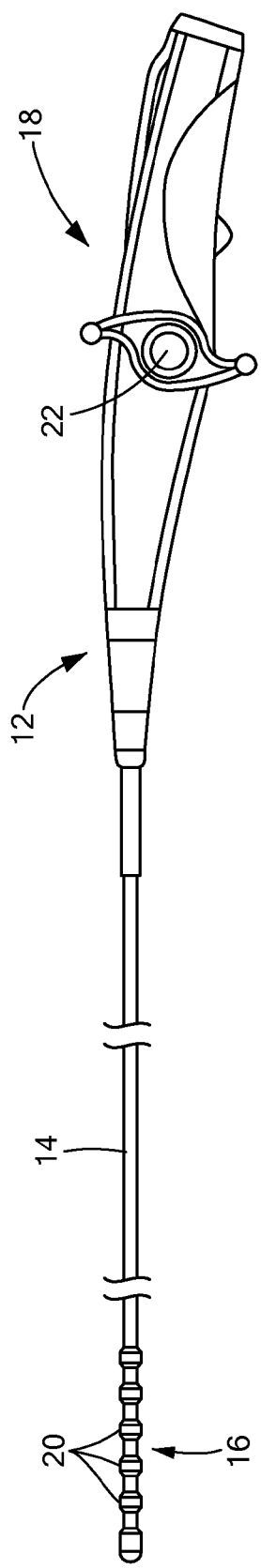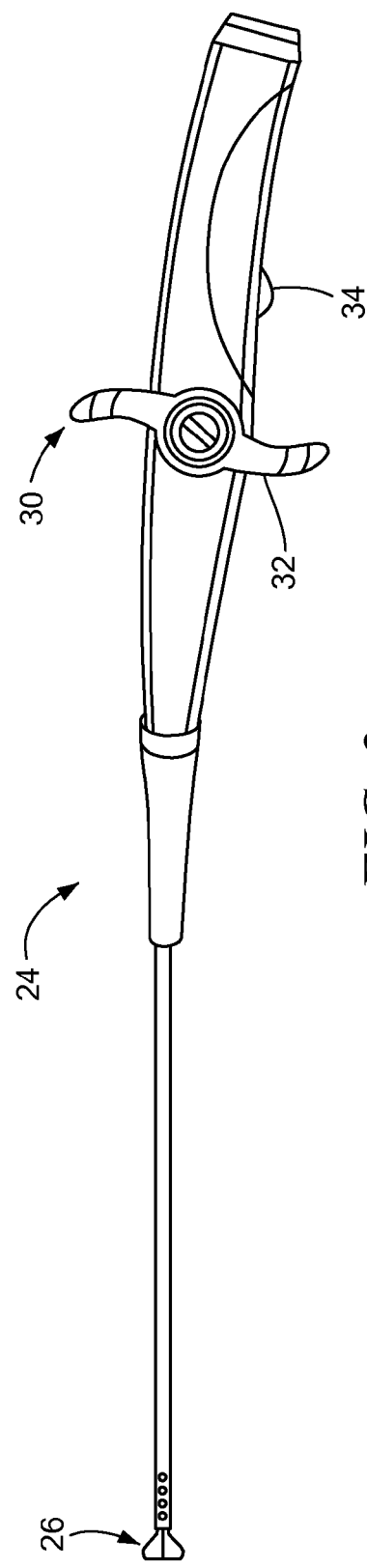

|  | Electrode 1 | | Electrode 2 | Electrode 9 | Electrode 10 | |
|---|---|---|---|---|---|---|
|  | % called low that are low | % in normal range called normal | % in normal range called normal | % in normal range called normal | % called low that are low | % in normal range called normal |
| 1 to 1 Mode |  |  |  |  |  |  |
| 140 | 95.8% | 99.8% | 99.8% | 99.4% | 98.3% | 99.9% |
| 150 | 99.5% | 99.3% | 99.2% | 97.0% | 99.9% | 99.3% |
| 160 | 99.9% | 97.7% | 97.5% | 89.1% | 100.0% | 95.7% |
| 2 to 1 Mode |  |  |  |  |  |  |
| 105 | 100.0% | 99.9% | 99.9% | 99.7% | 98.9% | 100.0% |
| 115 | 100.0% | 99.4% | 99.5% | 97.7% | 99.9% | 99.6% |
| 125 | 100.0% | 97.6% | 97.4% | 88.7% | 100.0% | 97.0% |
| 4 to 1 Mode |  |  |  |  |  |  |
| 70 | 94.3% | 100.0% | 100.0% | 99.9% | 94.2% | 100.0% |
| 80 | 99.8% | 99.8% | 99.8% | 99.3% | 99.8% | 99.9% |
| 90 | 100.0% | 98.4% | 98.1% | 95.0% | 100.0% | 98.7% |

*FIG. 12*

INTERMITTENT SHORT CIRCUIT DETECTION ON A MULTI-ELECTRODE CATHETER

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method for detecting short circuits between ablation electrodes during a radiofrequency ablation procedure.

BACKGROUND OF THE INVENTION

Current radiofrequency ablation ("RF") devices are constructed in a variety of configurations to target specific maladies and to provide for specific treatment protocols. In particular, many RF ablation devices have one or more treatment regions in which multiple treatment electrodes are disposed and are torqueable, or otherwise manipulatable, into a variety of different geometric configurations to treat particular cardiovascular tissues. For example, treatment electrodes may be coupled to an array or a carrier assembly manipulatable to define substantially linear, helical, and circular configurations depending on the desired treatment to be performed. In such configurations, each adjacent electrode may be spaced a distance away, whether longitudinal or radial, such that that bipolar or unipolar radiofrequency energy may be transmitted between the electrodes to treat the tissue.

Because the treatment electrodes may be manipulated into a variety of different positions, adjacent electrodes may be unintentionally positioned too close to one another such that a short circuit may occur. For example, when the electrode array is torqued to define a substantially circular configuration, when a distal electrode in the array is torqued and manipulated toward a proximal electrode in the array to define a circle, depending on the skill of the surgeon, the array may be over-manipulated such that two or more electrodes may intermittently touch each other, or be positioned sufficiently close such that the flow of current between the electrodes shorts, resulting in treatment safety concerns.

Current methods of detecting short circuits in electrosurgical devices involve measuring impedance between the electrodes with a tissue to be treated sandwiched between them like a clamp, and measuring when the impedance rises above a predetermined value. When the impedance threshold is reached, the entire electrosurgical device is deactivated. However, such methods result in an all or nothing response to a short circuit and do not allow for deactivation of the particular shorted electrodes while keeping activated non-shorted electrodes. Further, because many different energy modes may be utilized during an RF ablation treatment, a single static impedance threshold value may be inaccurate for certain energy modes. Other methods include measuring the temperature at the electrodes and detecting a short between electrodes if the temperature of one of the electrodes exceeds a temperature threshold when the power is less than predetermined valve. This existing short circuit algorithm may detect excessive temperatures on the electrode during a short circuit, but does not always detect a short circuit when electrodes are close together since high temperatures normally occur between the electrodes.

Accordingly, what is needed is a method of a short-circuit detection that facilitates the on-off operation of individual electrodes in an electrode array that is specific to a particular energy delivery mode.

SUMMARY OF THE INVENTION

The present invention advantageously provides a method and system for detecting a short circuit during a radiofrequency ablation procedure. The method includes measuring an impedance of a pair of electrodes coupled to a treatment assembly of a medical device. Radiofrequency ablation energy is transmitted between the pair of electrodes. The transmission of radiofrequency ablation energy between the pair of electrodes is terminated when after a predetermined period of time the measured impedance in either of the electrodes in the pair of electrodes is below a predetermined threshold impedance value. An alert is generated indicating a short circuit between the pair of electrodes.

In another embodiment, the system includes a medical device having a treatment assembly, the treatment assembly having a plurality of electrode pairs, the treatment assembly being manipulatable to define a substantially circular geometric configuration. A control unit is included, the control unit is operable to: measure an impedance of a first pair of the plurality of electrode pairs; transmit radiofrequency ablation energy between the plurality of electrode pairs; terminate the transmission of radiofrequency ablation energy between the first pair of the plurality of electrode pairs when after a predetermined period of time the measured impedance in either of the electrodes in the first pair of the plurality of electrode pairs is below a predetermined threshold impedance value; and generate and alert indicating a short circuit between the pair of electrodes.

In yet another embodiment, the method includes positioning an electrode array of a medical device proximate a tissue to be treated, the electrode array defining a proximal end and distal end and having a plurality of electrode pairs spanning from the proximal end to the distal end. The electrode array is manipulated to define a substantially circular geometric configuration. An impedance of a first pair of the plurality of electrode pairs is measured, the first pair of the plurality of electrode pairs including the most proximal electrode in the electrode array and the most distal electrode in the electrode array. Radiofrequency ablation energy is transmitted between the plurality of electrode pairs. The transmission of radiofrequency ablation energy between the first pair of the plurality of electrode pairs is terminated when after a predetermined period of time the measured impedance in either of the electrodes in the first pair of the plurality of electrode pairs is below a predetermined threshold impedance value. An alert is generated indicating a short circuit between the first pair of the plurality of electrode pairs.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a side view of an exemplary medical device constructed in accordance with the principles of the present invention;

FIG. 3 is a side view of another exemplary medical device constructed in accordance with the principles of the present invention;

FIG. 12 is a chart based on the observed minimum impedance values shown in FIG. 11, showing an estimated percentage of time low impedance values are correctly identified using the highlighted thresholds.

DETAILED DESCRIPTION OF THE INVENTION

Figure 1:
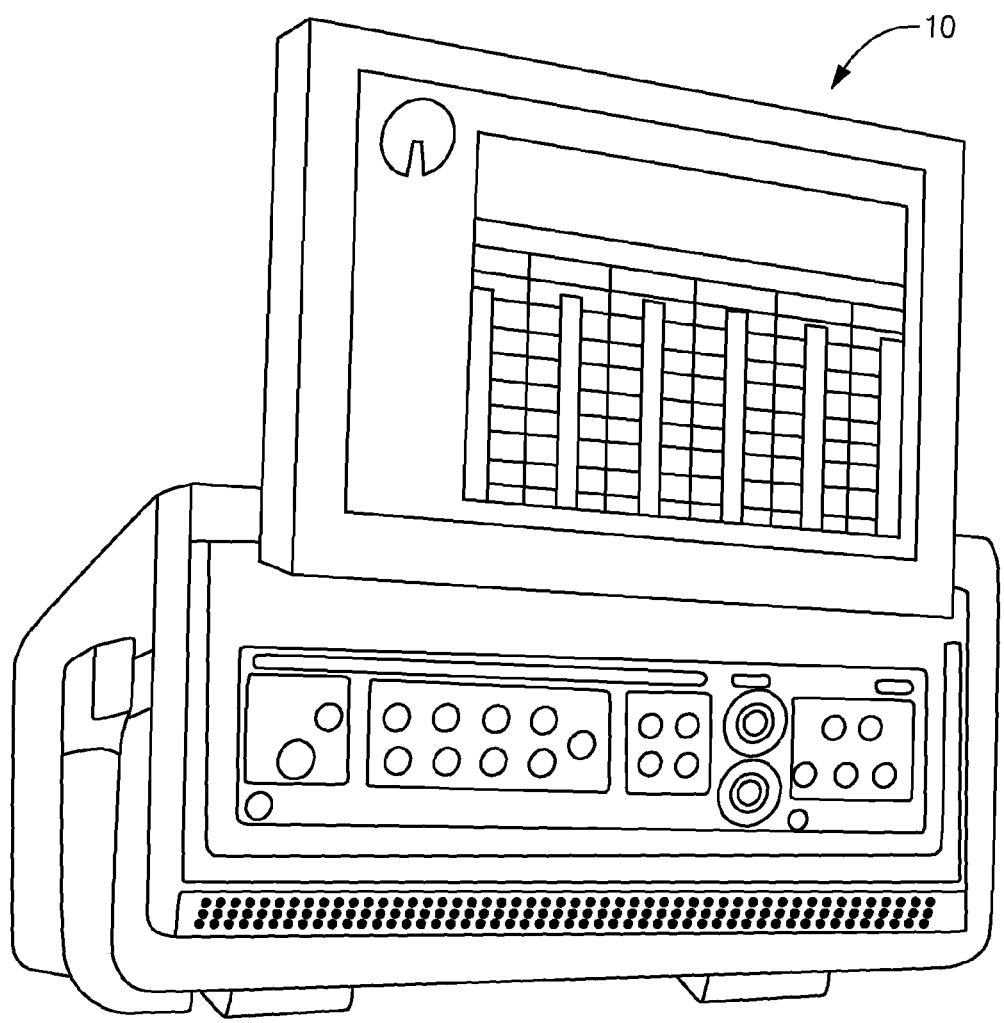
FIG. 1 is a perspective view of an exemplary control unit constructed in accordance with the principles of the present invention.

Referring now to the drawings in which like reference designators refer to like elements, there is shown in FIG. 1 an exemplary embodiment of a control unit such as for example an RF generator constructed in accordance with the principles of the present invention, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

The control unit 10 may generally include a display or monitor, operating controls, and couplings for connection to one or more medical devices, one or more patient return or "indifferent" electrodes, an ECG, a power cable, and/or other operating equipment. The control unit 10 may have electronic circuitry to produce the desired ablation energy, to deliver it to the ablation elements of a medical device, to obtain feedback information or parameters from other sensors, and to operate, adjust, modulate or cease providing the ablation energy during a medical treatment of a patient, as well as to display or otherwise inform the physician.

Generally, the control unit 10 may be operated in various modes which may be selected by the physician. For example, ablation energy may be supplied to one or more ablation elements, for example electrodes, in a bipolar mode, a unipolar mode, or a combination bipolar and unipolar mode. A unipolar mode of operation involves delivering energy between one or more ablation elements on a medical device and one or more patient return or reference electrodes touching the skin of the patient or positioned beneath the patient, such as a back plate. A bipolar mode of operation involves delivering energy between at least two electrodes on a medical device. A combination mode of operation involves delivering energy in both bipolar and unipolar modes simultaneously and/or intermittently. When in a combination mode of operation, it may be possible to select various ratios of activity or ablation energy among the bipolar and unipolar modes, including for example ratios such as 1:1, 2:1, or 4:1 (bipolar:unipolar). For example, an energy mode ratio of 4:1 means that four times more bipolar energy is transmitted between a pair of electrodes compared to unipolar energy transmitted.

The medical devices coupled to the control unit 10 may be catheters or surgical probes, including for example an electrophysiology catheter having diagnostic and/or treatment components positionable at or near a target tissue region. For example, the medical device 12 illustrated in FIG. 2 may have a shape and dimensions to reach various treatments sites, such as intraluminal access to vascular anatomy, including for example transseptal access to the left atrium of a patient's heart for subsequent treatment or ablation. The medical device 12 may generally define an elongated, flexible catheter body 14 having a distal treatment assembly 16, as well as a handle assembly 18 at or near a proximal end of the catheter body. The distal treatment assembly 16 may, for example, include one or more ablation elements such as electrodes 20, each of which may be electrically coupled to the control unit 10. The distal treatment assembly 16 of the medical device 12 may have a linear shape, with a plurality of ablation elements or electrodes 20. The catheter body 14 may be both flexible and resilient, with sufficient column strength facilitating steady contact with tissue, which improves signal fidelity in diagnosing contacted tissue as well as improve therapeutic thermal exchange between the device and contacted tissue. The proximal handle assembly 18 has a rotational actuator 22 for manipulating, bending, steering and/or reshaping the distal treatment assembly 16 into various desired shapes, curves, etc.

Figure 4:
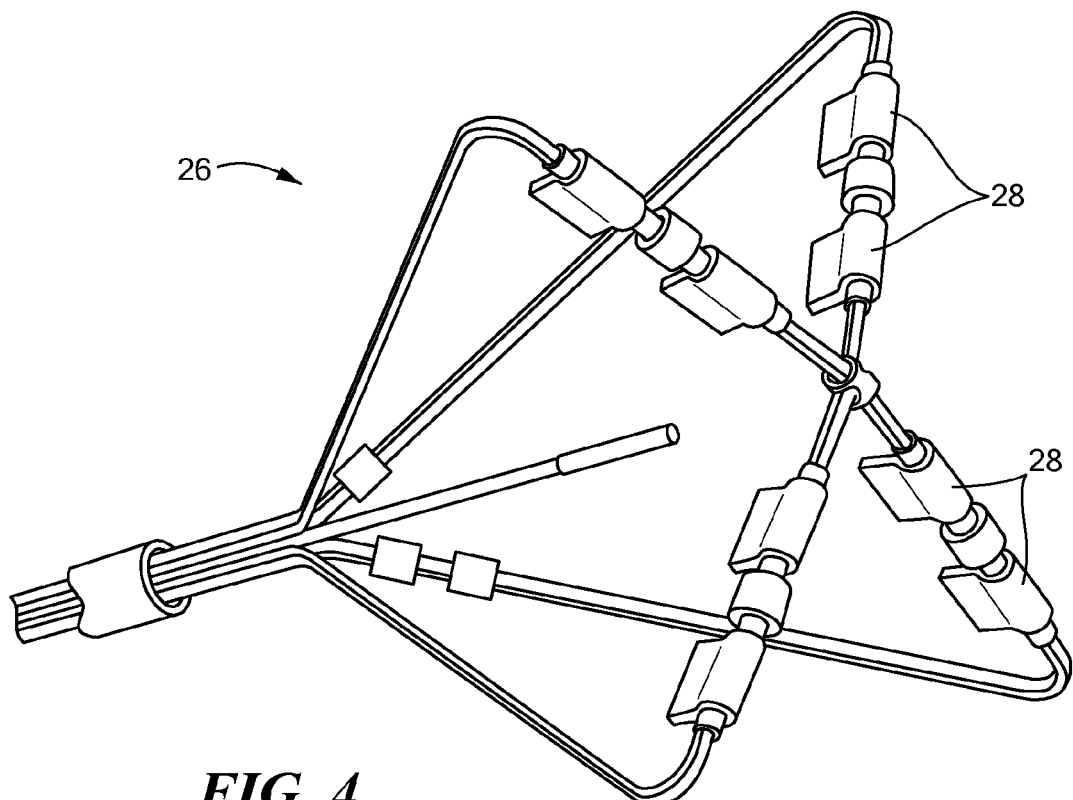
FIG. 4 is a perspective view of an exemplary treatment assembly of a medical device constructed in accordance with the principles of the present invention.
Figure 5:
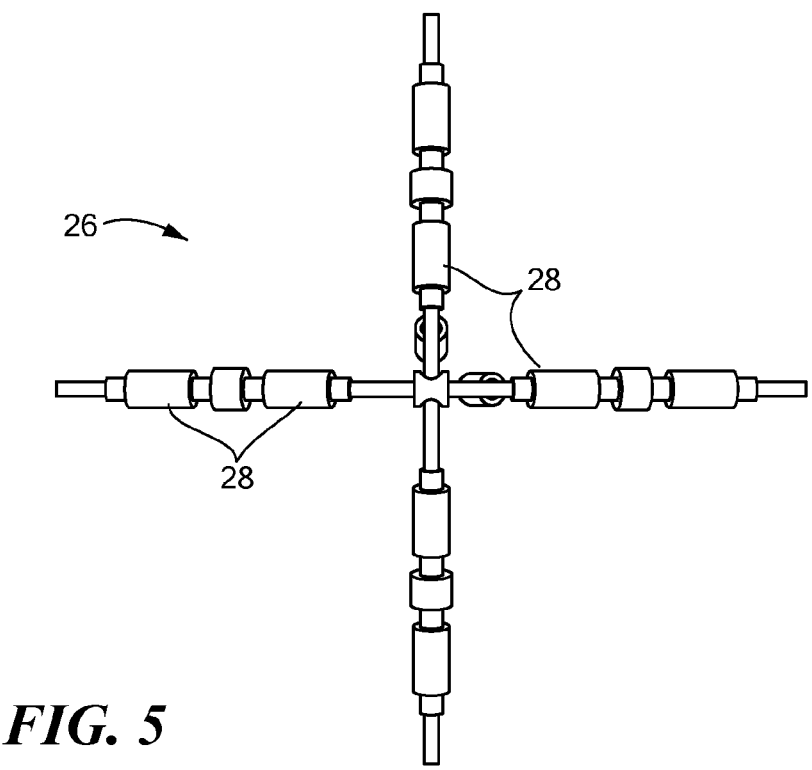
FIG. 5 is a front view of the treatment assembly shown in FIG. 4.

FIGS. 3-5 show a medical device or ablation catheter 24 with a catheter shaft and a distal treatment assembly 26 with compound carrier arms or electrode arrays which may be resilient, so that in a deployed configuration the electrodes 28 have a generally planar arrangement. Similar to the medical device 12 of FIG. 2, the distal treatment assembly 26 may be used for bipolar ablation, unipolar ablation, or a combination thereof. A proximal handle 30 has a rotational actuator 32 for manipulating a distal portion of the ablation catheter, and a linear actuator 34. The linear actuator 32 can advance the distal treatment assembly 26 distally beyond the catheter shaft, and retract the distal treatment assembly 26 proximally inside the catheter shaft. When the distal treatment assembly 26 is advanced distally, it may resiliently expand from a compressed arrangement inside the catheter shaft to the deployed arrangement shown in FIGS. 4 and 5.

Figure 6:
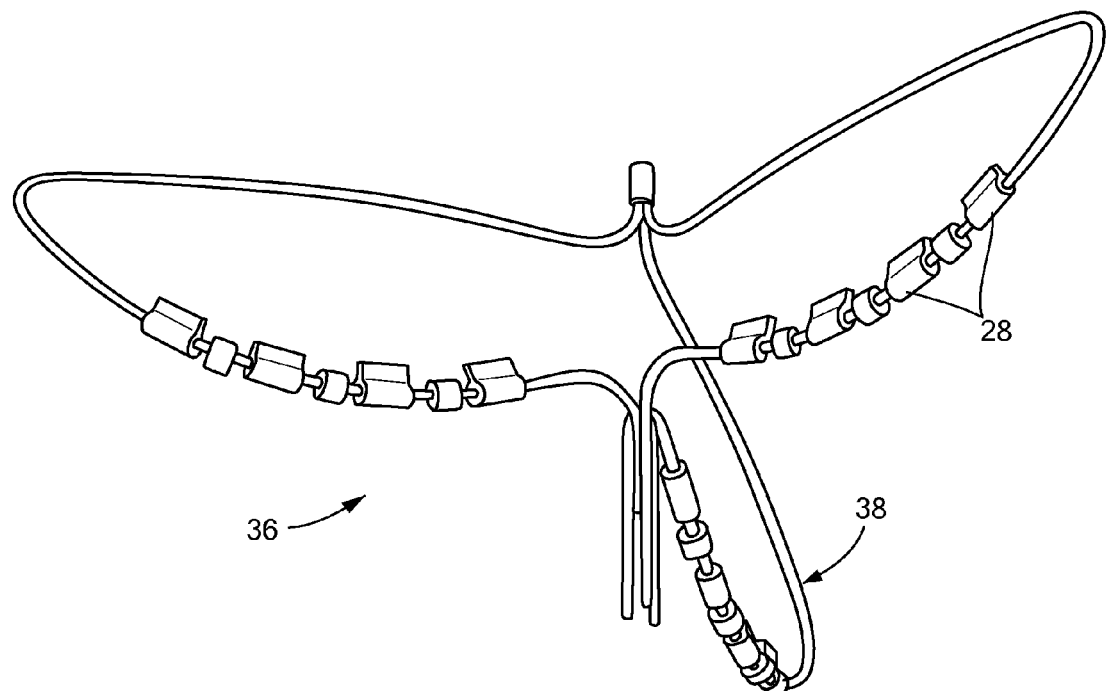
FIG. 6 is a perspective view of the treatment assembly of the medical device shown in FIG. 3.
Figure 7:
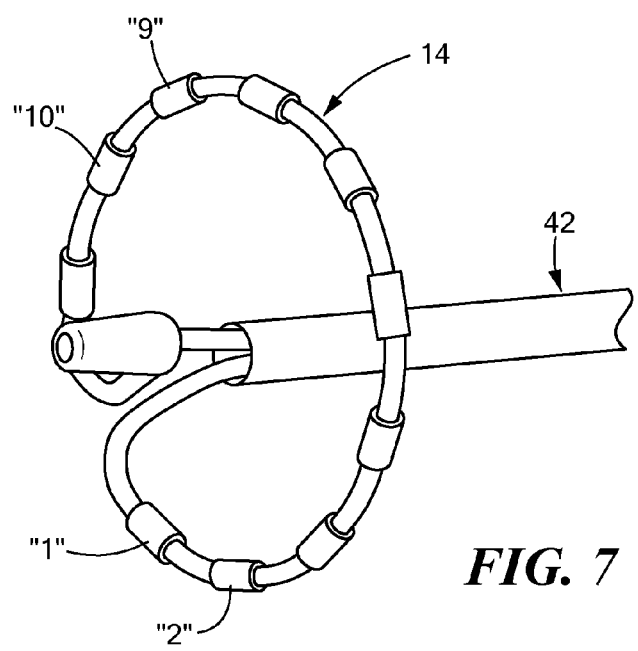
FIG. 7 is a perspective view of another exemplary treatment assembly of a medical device constructed in accordance with the principles of the present invention.

FIG. 6 shows a distal treatment assembly portion of a medical device or catheter 36 which has a resilient framework of carrier arms 38, in which the electrodes 40 have a proximally-directed configuration, which may for example be used for transseptal treatments of a patient's heart. Another distal treatment assembly portion of a medical device or catheter 42 is depicted in FIG. 7, which has a distal electrode array 44 with a plurality of electrodes 46 coupled to the array 44. The distal electrode array 44 may be manipulated to define a substantially linear, helical, or circular configuration, such that linear or substantially circumferential ablation lesion may be created during an ablation procedure.

Figure 8:
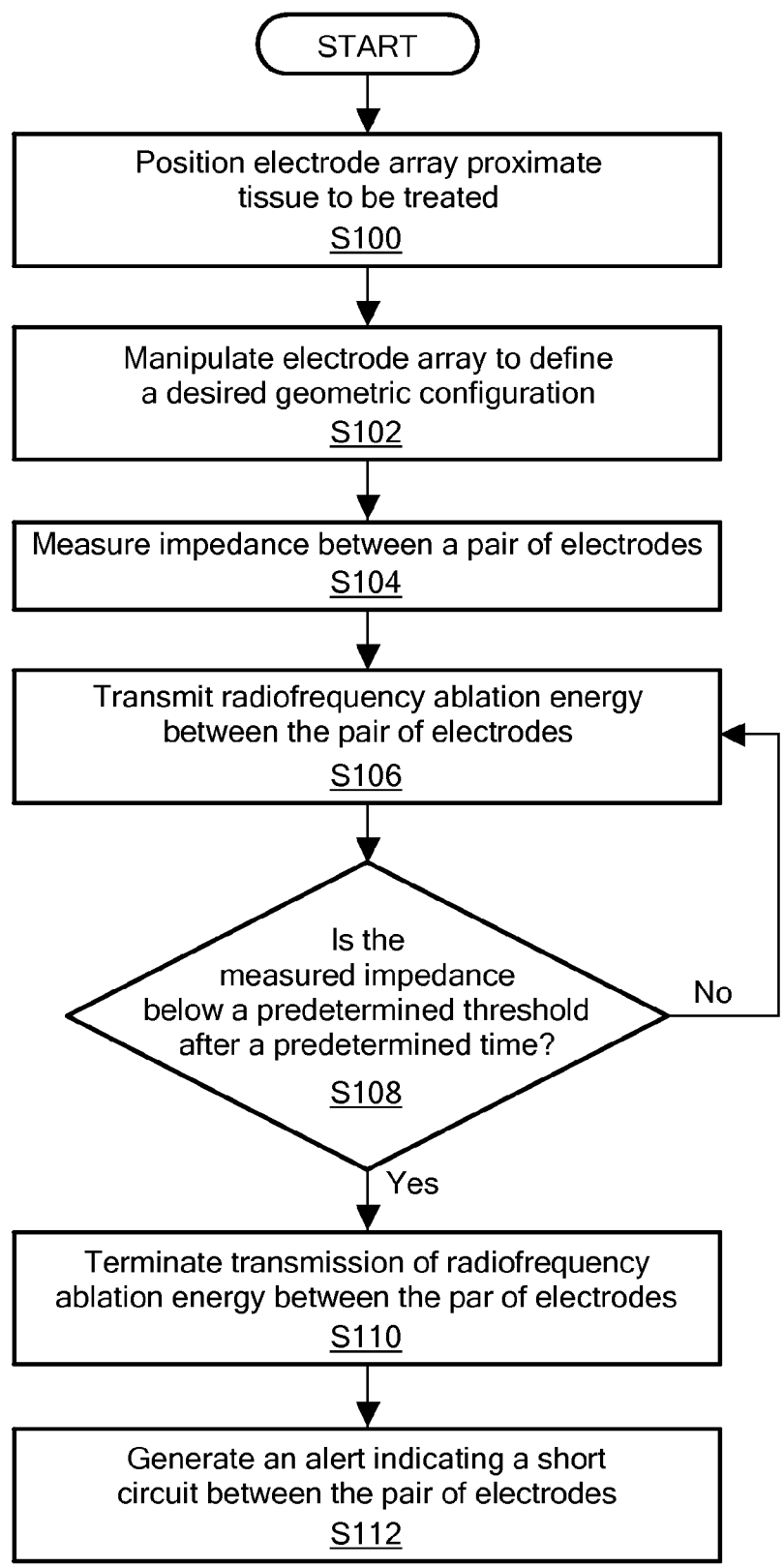
FIG. 8 is an exemplary method of determining a short circuit in an electrode in accordance with the principles of the present invention.

Now referring to FIG. 8 in which exemplary method of detecting a short circuit between a pair of electrodes is shown. The distal treatment assembly 16 of medical device 42, or any electrosurgical catheter, such as the medical devices discussed above, may be navigated through the vasculature toward a desired area of treatment, for example, the pulmonary vein. (Step S100). The treatment assembly may then be manipulated to a desired geometric configuration (Step S102). For example, the medical device 42 may include the electrode array 44, the electrode array 44 being manipulatable to define a substantially linear, helical, or circular configuration. In an exemplary configuration, the electrode array 44 includes ten electrodes 46 spaced a predetermined distance away from each on the array 44. The electrode 46 proximate the proximal end of the electrode array 44 when configured into a substantially linear configuration is referred to herein as electrode "1." The electrode 46 proximate the distal end of the electrode array 44 when configured into a substantially linear configuration is referred to herein as electrode "10." Electrodes 2-9 are disposed between electrodes 1-10, electrode 2 being adjacent electrode 1 and electrode 9 being adjacent electrode 10, and so on. In particular, when the electrode array 44 defines a substantially circular configuration shown in FIG. 7, electrodes 1 and 10 may be substantially radially adjacent each other along the electrode array 44.

Continuing to refer to FIG. 8, an impedance of a pair of the electrodes on the array 44 may be measured (S104). Each electrode 46 of the pair of the electrodes may be coupled to the array 44 or one electrode may be coupled to the array 44 and a second electrode may be coupled to the treatment assembly of a second medical device electrically coupled to the control unit. In such a configuration, the two medical devices may be positioned proximate the tissue to be treated and their respective electrodes may be activate to transmit radiofrequency energy. The impedance of electrodes 1 and 10, or 2 and 9, or so on, or every electrode 46 on the array 44, may be measured and calculated based on the duty cycle and the power supplied by the control unit 10. In an exemplary calculation, the duty cycle is the voltage. The measured impedance may then be calculated by squaring the voltage and dividing that value by the average power. To calculate the voltage the duty cycle may be divided by the preset number of fields, for example, 255, to arrive at the percentage of the duty cycle rather than a binary value. The impedance may be measured across all the electrodes 46, some of the electrodes 46, or particular pairs of electrodes depending on the particular geometric configuration defined for the particular ablation treatment.

Figure 9:
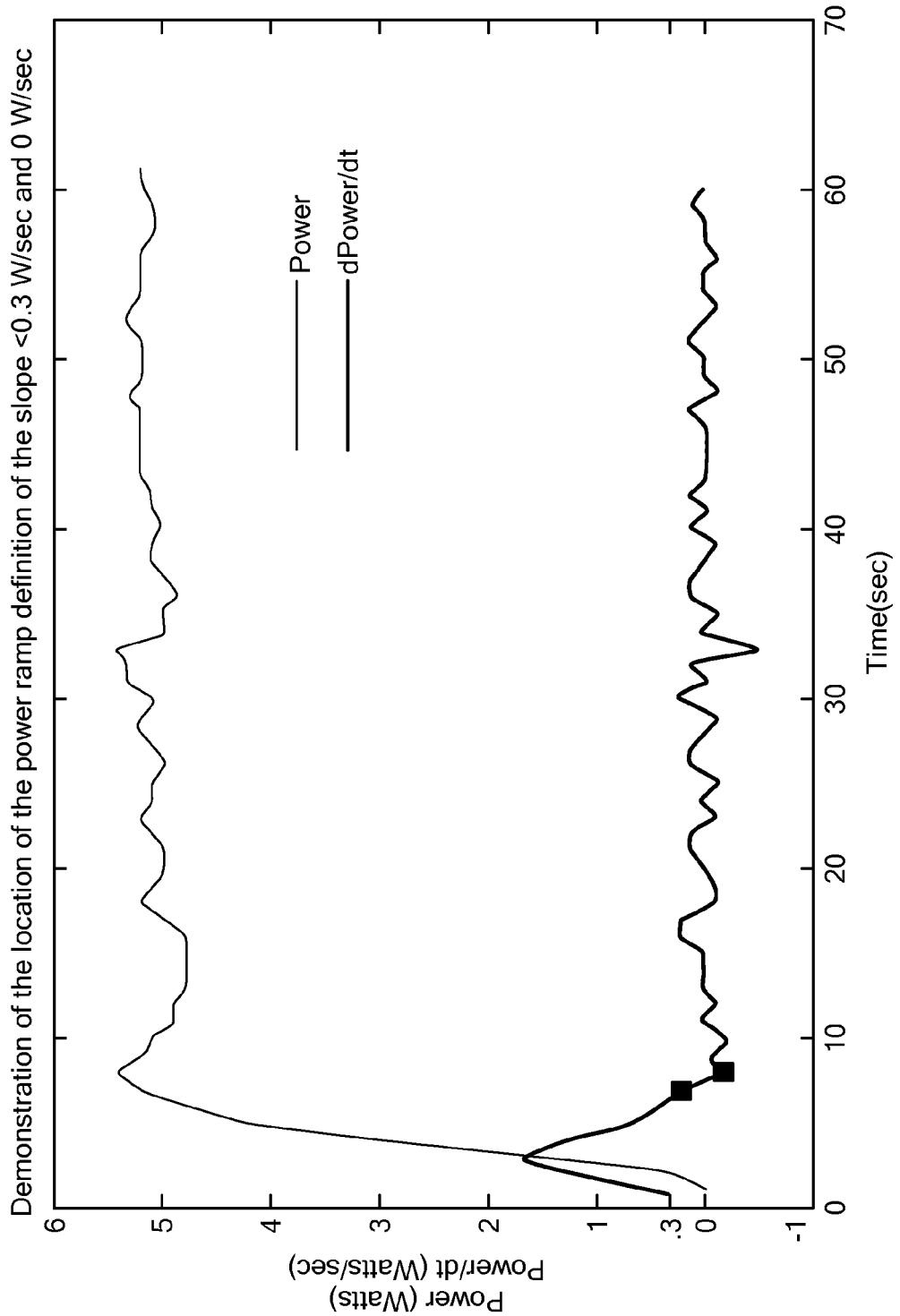
FIG. 9 is a graph showing the measured power over time and the derivative the power with respect to time to determine the ramp-up times.
Figure 10:
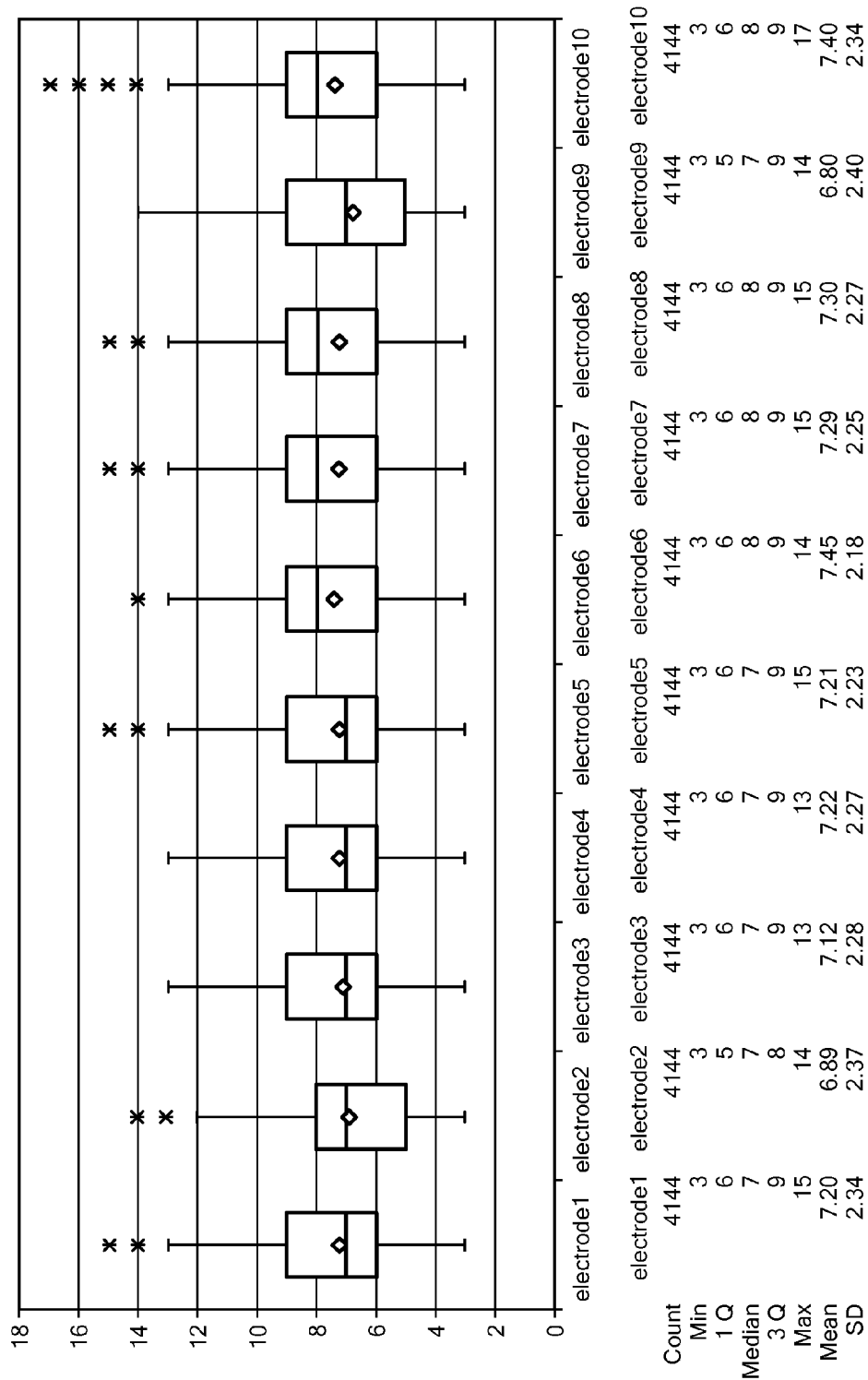
FIG. 10 is a box and whisker plot showing the median time to power plateau in 4144 ablation data sets, per electrode.

Radiofrequency ablation energy may be transmitted between two or more of the electrodes 46 on the array 44 and/or between the electrodes 46 and a reference electrode for a predetermined period of time (S106). For example, radiofrequency ablation energy may be transmitted between electrodes 1 and 10, and/or 2 and 9, and so on, in unipolar, 1:1, 2:1, 4:1, and/or bipolar energy modes. The impedance in Step S104 may be measured before, during, and/or after radiofrequency ablation energy is transmitted between the electrodes 46. After a predetermined period of ablation time, referred to herein as the ramp-up time, the measured impedance may be compared against a threshold or relative impedance value to determine if there is a short circuit between two electrodes (S108). In particular, to determine the ramp-up time, an analysis of the ramp-up time on over 4000 ablations was completed. As the temperature reaches a preprogrammed temperature set point, or the power reaches the maximum, the derivative of the power slows down and eventually crosses zero as seen in the plot in FIG. 9. The time to the derivative<0.3 Watts/second is used as a threshold to determine when the ramp up phase is completed. For example, as shown in FIG. 10, the median value for the ramp-up time is 7 seconds and the quartiles are at 6 and 9 seconds.

Figure 11:
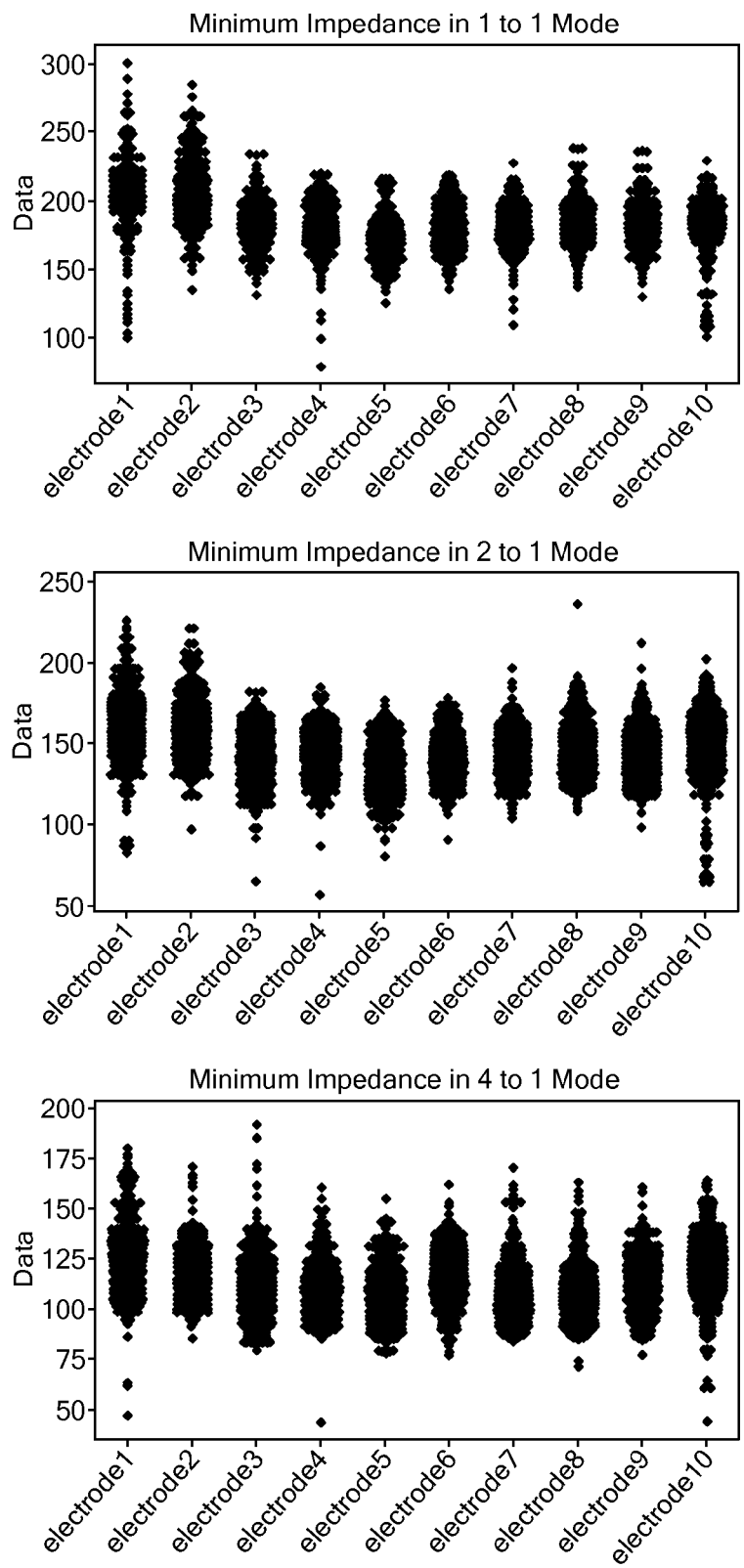
FIG. 11 are three scatter plots showing the minimum impedance values measured for electrodes in 1:1, 2:1, and 4:1 modes respectively, in the 4144 ablation data sets of FIG. 10.

The same roughly 4000 clinical ablations discussed above were further analyzed to determine threshold impedance values to determine if an intermittent short circuit has occurred between two or more electrodes 46 on the array 44 when manipulated into a substantially circular configuration. Owing to the different ratios of bipolar and unipolar energy that may be transmitted between the electrodes 46 and/or to a reference electrode, the more bipolar component of the energy mode, the lower the threshold impedance values. For example, an absolute threshold value was selected rather than a proportion of the starting impedance because the measured impedance from when ablation energy is initially transmitted may be too low, so detecting a drop in impedance may not accurately detect short circuits. The minimum impedance after 10 seconds of ablation time was calculated for each of the energy modes. The probability plots shown in FIG. 11 demonstrate that electrode 5 follows the expected normal distribution, since there are no instances of short circuits on electrode 5, whereas electrodes 1 and 10 have several outlier points for low impedance (points that fall away from the straight line representing the normal-distribution model). Thus, the outlier points on electrodes 1 and 10 may be used as a basis to determine when a short occurs in a particular electrode 46.

Now referring to FIG. 12, the chart shows the estimated percentage of time low impedance values will be correctly identified as short circuits using the highlighted thresholds of 150 ohms in 1:1 mode, 115 ohms in 2:1 mode, and 80 ohms in 4:1 mode, for electrodes 1 and 10, the electrodes 46 most likely to short during a procedure. Although not shown in FIG. 12, the threshold range for a bipolar energy mode only is between 35 and 55 ohms, with 45 ohms being an exemplary threshold. As illustrated in FIG. 12, should the measured impedance drop to a value+−10 ohms for the highlighted threshold, short circuits in electrodes 1 and 10 are correctly identified with over 95% accuracy.

If the measured impedance at any one of the electrodes 46 drops below the impedance threshold value or the relative impedance value for the particular energy mode, the flow of radiofrequency energy to the particular electrode 46 and/or electrode pair, for example, electrodes 1 and 10, may be selectively terminated (S110), while the other electrodes 46 in the array 44 may continue to transmit radiofrequency energy. Alternatively, in response to an intermittent short circuit with any of the electrodes 46, radiofrequency ablation energy may be terminated to the entire electrode array 44. If the measured impedance is above the threshold for the particular energy mode, then radiofrequency ablation energy may continue to be transmitted to the target tissue. An alert may be generated indicating a short circuit between the pair of shorted electrodes (Step 112). For example, the control unit 10 may display or otherwise alert the operator which electrodes are shorted and when the transmitting of radiofrequency energy between the shorted electrodes was terminated. Optionally, the measured impedance may also be compared against average measured impedances for a particular procedure and for a particular tissue. For example, in certain procedures and tissues, the starting measured impedance may be lower or higher depending on the thickness of the tissue to be ablated. Thus, in addition to comparing the measured impedance of a particular electrode to the predetermined threshold, the measured impedance may be compared to an average impedance for that particular tissue to further determine if a short circuit has occurred between two electrodes. For example, if the measured impedance drops below a predetermined percentage, for example, 80% below the mean measured impedance over time, which may be a dynamic mean, then a short circuit may have occurred between two electrodes.

The control unit 10 may be programmed to perform the various operations and calculate the measured impedances as discussed above. Specifically, the control unit 10 may automatically terminate to the flow of radiofrequency energy to the electrodes 46 or electrode pairs with measured impedance values below the predetermined threshold. Alternatively, the control unit 10 may display a visual warning or emit and audio warning when the measured impedance drops below the threshold such that the operator of the control unit 10 may manually terminate the flow of radiofrequency energy to the affected electrodes 46. Although the method and system described above is described with respect to a distal treatment assembly being configured to define a substantially circular geometric configuration, it is contemplated that the method and system described herein may be used with any configuration of electrodes and distal assemblies in which a short circuit may occur.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of detecting a short circuit during a radiofrequency ablation procedure, comprising:
    transmitting radiofrequency ablation energy to a pair of electrodes in at a monopolar and a bipolar mode, the radio frequency ablation energy being transmitted between at least one of a pair of electrodes coupled to a treatment assembly of a medical device when the radiofrequency ablation energy is transmitted in bipolar mode and between an electrode coupled to the treatment assembly of the medical device and a reference electrode when the radiofrequency ablation energy is transmitted in unipolar mode;
    wherein the transmitting of radio frequency ablation occurs at a ratio of bipolar mode to unipolar mode;
    measuring an impedance value of the pair of electrode for each of the energy modes; comparing the measured impedance value measured at each of the energy modes to a predetermined threshold impedance after the radiofrequency ablation energy has been transmitted for a predetermined period of time; and
    continuing the transmitting radiofrequency ablation energy if the measured impedance value in either of the electrodes in the pair of electrodes is above the predetermined threshold impedance and terminating the transmission of radiofrequency ablation energy and generating an alert indicating a short circuit between the pair of electrodes if the measured impedance in either of the electrodes in the pair of electrodes is below the predetermined threshold impedance value, the predetermined threshold value based on the ratio of radiofrequency ablation transmitted in the bipolar mode to radiofrequency ablation energy transmitted in the unipolar mode.

2. The method of claim 1, wherein the predetermined time period is between approximately 5 and 10 seconds.

3. The method of claim 1, wherein the ratio of radiofrequency ablation energy transmitted in bipolar mode to radiofrequency energy transmitted in unipolar mode is 1:1, and the predetermined impedance threshold is between approximately 140 and 160 ohms.

4. The method of claim 1, wherein the ratio of radiofrequency ablation energy transmitted in bipolar mode to radiofrequency energy transmitted in unipolar mode is 2:1, and the predetermined impedance threshold is between approximately 105 and 125 ohms.

5. The method of claim 1, wherein the ratio of radiofrequency ablation energy transmitted in bipolar mode to radiofrequency energy transmitted in unipolar mode is 4:1, and the predetermined impedance threshold is between approximately 70 and 90 ohms.

6. The method of claim 1, wherein the predetermined impedance threshold is between approximately 35 and 55 ohms.

7. The method of claim 1, wherein the treatment assembly includes an electrode array, the electrode array including approximately 10 electrodes, and wherein the method further includes:
    transmitting radiofrequency ablation energy between electrodes on the electrode array other than between the pair of electrodes; and
    the termination of the transmission of radiofrequency ablation energy between the pair of electrodes is independent of the transmission of radiofrequency ablation energy between electrodes on the electrode array other than the pair of electrodes.

8. The method of claim 1, further including manipulating the treatment assembly to define a substantially circular geometric configuration.

9. The method of claim 8, wherein the pair of electrodes is not adjacent each other along the treatment assembly when the treatment assembly defines a substantially circular geometric configuration.

10. A medical system, comprising:
    a medical device having a treatment assembly, the treatment assembly having a plurality of electrode pairs, the treatment assembly being manipulatable to define a substantially circular geometric configuration;
    a reference electrode at a location other than on the medical device;
    a control unit operable to:
        transmit radiofrequency ablation energy in bipolar mode between the plurality of electrode pairs and transmit radiofrequency ablation energy in unipolar mode between at least one electrode of at least one of the plurality of electrode pairs and the reference electrode;
        wherein the transmitting of radio frequency ablation is configured to occur at a ratio of bipolar mode to unipolar mode;
        measure an impedance value of a first pair of the plurality of electrode pairs for each of the energy modes; compare the measured impedance value of each of the energy modes to a predetermined threshold impedance after the radiofrequency ablation energy has been transmitted for a predetermined period of time; and continue the transmission of radiofrequency ablation energy if the measured impedance in either of the electrodes in the first pair of the plurality of electrode pairs is above the predetermined threshold impedance and terminate the transmission of radiofrequency ablation energy between the first pair of the plurality of electrode pairs and generating an alert indicating a short circuit between the pair of electrodes if the measured impedance in either of the electrodes in the first pair of the plurality of electrode pairs is below the predetermined threshold impedance value, the predetermined threshold impedance value based on the ratio of the radiofrequency ablation energy transmitted in the bipolar mode to the radiofrequency ablation energy transmitted in the unipolar mode.

11. The system of claim 10, wherein the predetermined time period is 7 seconds.

12. The system of claim 10, wherein the ratio of radiofrequency ablation energy transmitted in bipolar mode to radiofrequency ablation energy transmitted in unipolar mode is 1:1, and the predetermined impedance threshold is approximately 150 ohms.

13. The system of claim 10, wherein the ratio of radiofrequency ablation energy transmitted in bipolar mode to radiofrequency ablation energy transmitted in unipolar mode is 2:1, and the predetermined impedance threshold is approximately 115 ohms.

14. The system of claim 10, wherein the ratio of radiofrequency ablation energy transmitted in bipolar mode to radiofrequency ablation energy transmitted in unipolar mode is 4:1, and the predetermined impedance threshold is approximately 80 ohms.

15. The system of claim 10, wherein the predetermined impedance threshold is approximately 45 ohms.

16. The system of claim 10, wherein the termination of the transmission of radiofrequency ablation energy between the first pair of the plurality of electrode pairs is independent of the transmission of radiofrequency ablation energy between electrode pairs on the electrodes array other than the first pair of the plurality of electrode pairs.

* * * * *

UNITED STATES PATENT AND TRADEMARK OFFICE
CERTIFICATE OF CORRECTION

PATENT NO.         : 9,060,778 B2                                    Page 1 of 1
APPLICATION NO.    : 13/456592
DATED              : June 23, 2015
INVENTOR(S)        : Catherine R. Condie and Marshall L. Sherman It is certified that error appears in the above-identified patent and that said Letters Patent is hereby corrected as shown below:

In the claims

In Column 7, line 41, Claim 1, after "electrodes in at" add --least one of--.

Signed and Sealed this
First Day of December, 2015

Michelle K. Lee
*Director of the United States Patent and Trademark Office*